United States Patent [19]

Yamane et al.

[11] Patent Number: 4,690,898

[45] Date of Patent: Sep. 1, 1987

[54] DNA CODING FOR A SIGNAL PEPTIDE AND DNA CONTAINING THE SAME

[75] Inventors: Kunio Yamane, 614-201, Takezono 3-chome, Sakura-mura, Niihari-gun, Ibaragi-ken; Kazutaka Ohmura, Chiba; Hisato Yamazaki, Hyogo; Teruaki Shiroza, Chiba, all of Japan

[73] Assignees: Kunio Yamane, Ibaragi; The Calpis Food Industry Co., Ltd., Tokyo; Daicel Chemical Industries, Ltd., Osaka; Oji Corn Starch Co., Ltd., Tokyo, all of Japan

[21] Appl. No.: 704,885

[22] Filed: Feb. 25, 1985

[30] Foreign Application Priority Data

Mar. 9, 1984 [JP] Japan ................................. 59-043826

[51] Int. Cl.⁴ ...................... C12N 1/00; C12N 15/00; C07H 17/00
[52] U.S. Cl. ..................................... 435/320; 536/27; 435/172.3; 935/48; 935/24; 935/27
[58] Field of Search ............... 435/317, 172.3; 935/14, 935/24, 48, 29; 536/27

[56] References Cited

PUBLICATIONS

Ohmura, K., et al., *Nuc. Acids Res.*, vol. 12, No. 3, pp. 5307–5319 (1984).
Ohmura, K., et al., *Biochem. Biophys. Res. Comm.*, vol. 112, No. 2, pp. 678–683 (Apr. 1983).
Yamazaki, H. et al., *J. Bacteriol*, vol. 156, No. 1, pp. 327–337, (Oct. 1983).
Ohmura, K., et al., *J. Biochem.*, vol. 95, pp. 87–93 (1984).

*Primary Examiner*—Thomas G. Wiseman
*Assistant Examiner*—Jayme A. Huleatt
*Attorney, Agent, or Firm*—Browdy and Neimark

[57] ABSTRACT

This invention relates to DNA consisting of a DNA base sequence coding for the signal peptide:

| Met | Phe | Ala | Lys | Arg | Phe | Lys |
|-----|-----|-----|-----|-----|-----|-----|
| Thr | Ser | Leu | Leu | Pro | Leu | Phe |
| Ala | Gly | Phe | Leu | Leu | Leu | Phe |
| Tyr | Leu | Val | Leu | Ala | Gly | Pro |
| Ala | Ala | Ala | | | | | and to DNA containing said DNA base sequence. The DNA base sequence coding for said signal peptide includes, for example;

| ATG | TTT | GCA | AAA | CGA | TTC | AAA |
|-----|-----|-----|-----|-----|-----|-----|
| ACC | TCT | TTA | CTG | CCG | TTA | TTC |
| GCT | GGA | TTT | TTA | TTG | CTG | TTT |
| TAT | TTG | GTT | CTG | GCA | GGA | CCG |
| GCG | GCT | GCG. | | | | |

The desired products in cells can be secreted out of cells by the use of a vector containing DNA consisting of the DNA base sequence coding for said signal peptide.

6 Claims, No Drawings

DNA CODING FOR A SIGNAL PEPTIDE AND DNA CONTAINING THE SAME

BACKGROUND OF THE INVENTION

This invention relates to DNA coding for a signal peptide which acts to secrete proteins out of cells and to a DNA containing said signal peptide.

The signal peptide herein means a peptide acting so that proteins formed in cells can be secreted out of the cells. Generally, proteins are produced in cells and accumulated therein. On the other hand, those proteins having a signal peptide are said to be secreted out of cells along with their formation therein. Accordingly, proteins formed in cells can be successfully secreted out of the cells if such a signal peptide is utilized.

Secretion of proteins out of cells could have the following advantages: Firstly, if proteins formed in cells can be moved out of the cells, it will become possible to readily separate contaminatings from the proteins, which reduces the labor required for the purification and isolation thereof. In addition, the proteins can be isolated in a pure state without any poisonous substances originating from the cell membrane, so that they will be widely available with no restriction. Secondly, even though the production of proteins would be inhibited by their own excessive formation, transfer thereof out of the biosynthetic system will free them from the feedback inhibition, which enables their excessive production. Thirdly, those proteins which deteriorates the growth of cells can be moved out of the cells which enables their production without inhibiting normal growth of the cells.

Several kinds of such signal peptides and DNA base sequences thereof have been known. For example, a signal peptide for penicillinase for *Bacillus licheniformis* (Nucleic Acid Research, Vol. 19, No. 11, 2577 (1981)) and a signal peptide for α-amylase for *Bacillus amyloliquefaciense* (Gene, 15, 43 (1981)) have been known.

The present inventors have carried out the cloning of α-amylase gene of *Bacillus subtilis* which has been known for its very high α-amylase productivity, analyzed the resulting cloned gene and found a novel signal peptide different from the known signal peptide and DNA base sequence thereof for amylase.

Production of proteins by the use of the DNA of the present invention in a host vector system wherein *Bacillus subtilis* of a high α-amylase productivity is employed as the host is superior in stability and secretion productivity to those by the use of other organisms or other signal peptides.

SUMMARY OF THE INVENTION

It is an object of the present invention to provide a novel DNA base sequence coding for a novel signal peptide consisting of

| Met | Phe | Ala | Lys | Arg | Phe | Lys |
|-----|-----|-----|-----|-----|-----|-----|
| Thr | Ser | Leu | Leu | Pro | Leu | Phe |
| Ala | Gly | Phe | Leu | Leu | Leu | Phe |
| Tyr | Leu | Val | Leu | Ala | Gly | Pro |
| Ala | Ala | Ala |     |     |     |     | said DNA base sequence being preferably as follows:

| ATG | TTT | GCA | AAA | CGA | TTC | AAA |
|-----|-----|-----|-----|-----|-----|-----|
| ACC | TCT | TTA | CTG | CCG | TTA | TTC |
| GCT | GGA | TTT | TTA | TTG | CTG | TTT |
| TAT | TTG | GTT | CTG | GCA | GGA | CCG |
| GCG | GCT | GCG. |   |   |   |   |

DETAILED DESCRIPTION OF THE PREFERRED EMBODIMENTS

The chemical symbols used in the present specification stand for the following compounds:

| Met | methionine |
| Phe | phenylalanine |
| Ala | alanine |
| Lys | lysine |
| Arg | arginine |
| Thr | threonine |
| Ser | serine |
| Leu | leucine |
| Pro | proline |
| Gly | glycine |
| Tyr | tyrosine |
| Val | valine |
| Glu | glutamic acid |
| Asn | asparagine |
| A | adenine |
| T | thymine |
| G | guanine |
| C | cytosine |

The DNA base sequence coding for various amino acids in the present invention is described below.

The bases listed below shall include modified bases such as methylated ones.

| Met | ATG |
| Phe | TTT, TTC |
| Ala | GCT, GCC, GCA, GCG |
| Lys | AAA, AAG |
| Arg | AGA, AGG, CGT, CGC, CGA, CGG |
| Thr | ACT, ACC, ACA, ACG |
| Ser | TCT, TCC, TCA, TCG, AGT, AGC |
| Leu | TTA, TTG, CTT, CTC, CTA, CTG |
| Pro | CCT, CCC, CCA, CCG |
| Gly | GGT, GGC, GGA, GGG |
| Tyr | TAT, TAC |
| Val | GTT, GTC, GTA, GTG |
| Glu | GAA, GAG |
| Asn | AAT, AAC. |

The various DNA base sequences coding for amino acids as listed above can be properly selected for the use in the present invention.

The DNA fragment consisting of a DNA base sequence coding for the signal peptide of the present invention and the DNA fragment containing the same may be chemically synthesized or extracted from the chromosomal DNA of certain strains.

The strains available in the latter method include, for example, *Bacillus subtilis* of a high α-amylase productivity. The *Bacillus subtilis* of high amylase productivity as cited herein includes those strains which have been improved by various means for a long time, such as *Bacillus subtilis* NA 64 strain (IA 412) prepared by incorporating an α-amylase controlling gene of *Bacillus natto* into *Bacillus subtilis* 6160 strain derived from *Bacillus subtilis* 168 strain. These strains are characterized by the ability to secrete a large amount of α-amylase out of cells. The NA 64 strain (IA 412) has been widespread and readily available, for example, from the Bacillus Genetic Stock Center of the Ohio State University. The NA 64 strain has been deposited with the Fermentation Research Institute, Agency of Industrial Science and Technology under the deposit number of FERM BP-423.

DNA fragments coding for the signal peptide of the present invention may be most preferably and rapidly prepared by a chemical synthesis such as a solid phase phosphotriester method.

In order to secrete the desired protein by ligating the gene of the protein to the DNA fragments of the present invention, labor-saving and convenience in the process of the preparation of hybrid DNA should be taken into account. That is to say, it is more efficient to directly prepare DNA fragments which contain DNA coding for the signal peptide, a promotor portion necessary for the gene expression and other required DNA than to prepare DNA coding for the signal peptide and subsequently link it with other required DNA fragments. If necessary, DNA linkers are useful to fuse DNA fragments. Examples of available DNA fragments containing DNA coding for the signal peptide of the present invention are as follows:

|   | C | TGGCTTACAG | AAGAGCGGTA |
|---|---|---|---|
| AAAGAAGAAA | TAAAAAGAA | ATCATCTTGA |
| AAAATAGATG | GTTTTTTTTT | TTGTTTGGAA |
| AGCGAGGGAA | ACAGTCTCGG | GCAGTTTTTT |
| ATAGGACCAT | TGATTTGTAT | TCACTCTGCC |
| AAGTTGTTTT | GATAGAGTGA | TTGTGATAAT |
| TTAAAATGTA | AGCGTAAACA | AAATTCTCCA |
| GTCTTCGCAT | CAGTTTGAAA | GGAGGAAGCG |
| GAAGAATGAA | GTAAGAGGGA | TTTTTGACTC |
| CGAAGTAAGT | CTTCAAAAAA | TCAAATAAGG |
| AGTGTCAAGA | ATGTTTGCAA | AACGATTCAA |
| AACCTCTTTA | CTGCCGTTAT | TCGCTGGATT |
| TTTATTGCTG | TTTTATTTGG | TTCTGGCAGG |
| ACCGGCGGCT | GCG. | |

When a base sequence coding for the signal peptide of the present invention is linked with a DNA base sequence coding for a protein to be secreted and incorporated into a strain with the use of an appropriate genetic expression promotor and a vector, the protein secreted out of cells has the normal N-terminal, which seems to result from the incision between the N-terminal of the desired protein and the C-terminal of the signal peptide of the present invention in the process of the secretion.

It has been found that the use of a DNA fragment which contains DNA coding for a signal peptide wherein another DNA sequence is added to the downstream, i.e., the side of the 3′-terminal of the DNA coding for the signal peptide of the present invention would sometimes bring about the secretion of a protein carrying the residual peptide corresponding to the added DNA sequence at the N-terminal out of the cells. In the case of those proteins comprising the desired protein and additional peptide, it is sometimes necessary to incise the additional peptide followed by purification to obtain the expression of the activity of the desired protein. Those proteins are non-preferable from a physiological viewpoint since they might result in some immunological troubles when inoculated into an organism as such.

DNA fragments which contain a DNA sequence coding for the signal peptide of the present invention would not exhibit these disadvantages as described above when utilized in a protein secretion system. It is one of the great characteristics of the present invention.

To illustrate the preparation of DNA fragments containing a DNA base sequence coding for the signal peptide of the present invention, and not by way of limitation, the following example will be given.

PREPARATION EXAMPLE

The α-amylase gene was prepared as follows: The chromosol DNA was prepared from Bacillus subtilis NA 64 strain (IA 412) (FERM BP-423) which produces α-amylase, an exocellular enzyme, by the Saito-Miura method (Saito, H., et al., Biochem. Biophys. Acta., 72, 619 (1963)).

The temperate phage ρ11 (Dean, D. H., et al., J. Virol., 20, 509 (1976)) was prepared as follows: ρ11 particles were obtained by inducing the lysogenic strain of temperate phage ρ11 by the treatment with mitomycin C (a product of Kyowa Hakko Kogyo Co., Ltd.).

The ρ11 was purified by the cesium chloride equilibrium density gradient centrifugation method, wherein the cesium chloride solution was set to a density of 1.51 g/cm$^3$ prior to the centrifugation. DNA was prepared from the purified ρ11 particles by SDS/phenol/ethanol precipitation.

The chromosomal DNA prepared from Bacillus subtilis NA 64 strain and the ρ11 DNA obtained in the above-mentioned manner were incised with a restriction enzyme Bam HI (a product of Takara Shuzo Co., Ltd.) and subsequently linked with T4-ligase (a product of Takara Shuzo Co., Ltd.), from which specifically transduced phage particles retaining the α-amylase gene were obtained by the method of Kawamura et al. (Gene, 5, 87 (1979)) or the method of Nomura et al. (Agric. Biol. Chem., 43, 2637 (1979)). The resulting specifically transduced phage particles retaining the α-amylase gene were further processed into ρ11 DNA retaining the α-amylase gene by SDS/phenol/ethanol precipitation.

The ρ11 DNA thus obtained was partially digested with a restriction enzyme Sau 3A (a product of Takara Shuzo Co., Ltd.). The resultant was linked with a plasmid pUB 110 fragment incised with the restriction enzyme Bam HI By the use of T4 ligase to give a hybrid plasmid mixture.

Bacillus subtilis was transformed by the use of this mixture according to the protoplast transformation method (Chang, S., and Cohen, S. N., M. G. G., 168, 111 (1979)). Among the transformed strains, those exhibiting resistance to a kanamycin (10 μg/ml) and activity of α-amylase were selected. These selected strains were grown on a kanamycin-containing medium (10 μg/ml) and then plasmids retained in the cultured cells were prepared by the conventional cleared lysate method. The resulting plasmids were incised with restriction enzymes Eco RI (a product of Takara Shuzo Co., Ltd.) and Xba I (a product of Takara Shuzo Co., Ltd.) and the products were subjected to 0.8% agarose gel electrophoresis. Then DNA fragments corresponding to approximately 1.4 Kbp were extracted from the gel according to the hydroxyapatite method (Tabak, H. F., and Flavell, R. A., Nucleic Acids R., 5, 2321 (1978)). This fragment was further incised with a restriction enzyme Alu I (a product of Takara Shuzo Co., Ltd.) and subjected to 5% polyacrylamide gel electrophoresis to cut out a band of approximately 0.43 Kbp. Thus DNA of approximately 0.43 Kbp was extracted by the use of an extraction buffer (0.1M tris HCl; pH=8.0), 0.5M ammonium acetate and 10 mM EDTA.

The DNA fraction of approximately 0.43 Kbp thus obtained was further incised with a restriction enzyme Hpa II (a product of Takara Shuzo Co., Ltd.) and subjected to 5% polyacrylamide electrophoresis to thereby extract and purify a DNA fraction of approximately 0.38 Kbp. Separately 5'-CGGCGGCTGCGCA-3'(13-mer) and 3'-CGCCGACGCGTTCGA-5'(15-mer) were chemically synthesized by the solid phase phosphotriester method.

Each 5'-terminal was phosphorylated with T4 trinucleotide kinase (a product of Takara Shuzo Co., Ltd.) in a conventional manner. These DNA fragments were mixed with each other in an equimolar ratio and subjected to conventional annealing to give a double-stranded DNA fragment. This DNA fragment was mixed with the DNA fragment of approximately 0.38 Kbp as prepared above in a ratio of 20:1 and the mixture was linked with T4 ligase in a conventional manner, incised with a restriction enzyme Hind III (a product of Takara Shuzo Co., Ltd.) and subjected to 5% polyacrylamide gel electrophoresis followed by extraction of the corresponding fragment of approximately 0.40 Kbp from the gel. Synthetic DNA was added to the Hpa II site by this treatment to give a novel Hind III-sited DNA fragment. Thus the DNA fragment containing the DNA coding for the signal peptide as intended in the present invention was obtained.

The fact that this DNA fragment could code the amino acid sequence as intended in the present invention was confirmed by the analysis of the fragment by the Maxam-Gilbert method (Method in Enzymology, vol. 65, 499).

It was further confirmed that the fragment contained the DNA sequence coding for the signal peptide of the present invention as shown below as well as the linker portion at one terminal.

| | | | | | | |
|---|---|---|---|---|---|---|
| 5'-ATG | TTT | GCA | AAA | CGA | TTC | AAA |
| TAC | AAA | CGT | TTT | GCT | AAG | TTT |
| ACC | TCT | TTA | CTG | CCG | TTA | TTC |
| TGG | AGA | AAT | GAC | GGC | AAT | AAG |
| GCT | GGA | TTT | TTA | TTG | CTG | TTT |
| CGA | CCT | AAA | AAT | AAC | GAC | AAA |
| TAT | TTG | GTT | CTG | GCA | GGA | CCG |
| ATA | AAC | CAA | GAC | CGT | CCT | GGC |
| GCG | GCT | GCG | CA-3' | | | |
| CGC | CGA | CGC | GTT | CGA. | | |

There was a promotor portion derived from α-amylase and necessary for the expression at the upstream of the 5'-terminal of this sequence. The 3'-terminal of the above-mentioned sequence corresponded to one terminal of the DNA fragment containing the DNA coding for the signal peptide. This 3'-terminal contained the DNA sequence corresponding to the Hind III linker in order to readily carry out the following experiment.

EXPERIMENTAL EXAMPLE

1. Preparation of B-41

A DNA fragment of approximately 0.43 Kbp and incised with Alu I was prepared in the same manner as described in Preparation Example.

This fragment and the Hind III linker (a product of Takara Shuzo Co., Ltd.) were linked with T4 ligase (a product of Takara Shuzo Co., Ltd.) in a conventional manner, incised with a restriction enzyme Hind III (a product of Takara Shuzo Co., Ltd.) and thereafter subjected to 5% polyacrylamide gel electrophoresis to thereby extract said fragment of approximately 0.43 Kbp linked with the Hind III linker from the gel.

The sequence of this fragment was confirmed by the analysis according to the Maxam-Gilbert method (Method in Enzymology, vol. 65, 499).

It was further confirmed that one end of this fragment partially contained the DNA coding for the following signal peptide of the present invention:

| | | | | | | |
|---|---|---|---|---|---|---|
| 5'-ATG | TTT | GCA | AAA | CGA | TTC | AAA |
| TAC | AAA | CGT | TTT | GCT | AAG | TTT |
| ACC | TCT | TTA | CTG | CCG | TTA | TTC |
| TGG | AGA | AAT | GAC | GGC | AAT | AAG |
| GCT | GGA | TTT | TTA | TTG | CTG | TTT |
| CGA | CCT | AAA | AAT | AAC | GAC | AAA |
| TAT | TTG | GTT | CTG | GCA | GGA | CCG |
| ATA | AAC | CAA | GAC | CGT | CCT | GGC |
| GCG | GCT | GCG | AGT | GCT | GAA | ACG |
| CGC | CGA | CGC | TCA | CGA | CTT | TGC |
| GCG | AAC | AAA | TCG | AAT | GAG | CA-3' |
| CGC | TTG | TTT | AGC | TTA | CTC | GTT | CGA |

There was a promotor portion derived from α-amylase and necessary for the expression at the upstream of the 5'-terminal of this sequence. The 3'-terminal of the above-mentioned sequence corresponds to one terminal of the DNA fragment of approximately 0.43 Kbp which contained the DNA coding for the signal peptide. The DNA base sequence coding 31 amino acids from the 5'-terminal of the above sequence is identical with that of B-31. That is, the above sequence comprises B-31 to which another DNA sequence is added at the 3'-terminal. This fragment will be referred to as B-41 hereinbelow. Similar to B-31, B-41 further contains a DNA sequence corresponding to the Hind III linker at the 3'-terminal in order to carry out the following experiment readily.

2. Preparation of a vector and a gene fragment coding for an ampicillin-decomposing enzyme.

Plasmid pUB 110 was employed as a vector while an ampicillin-decomposing enzyme derived from plasmid pBR 322 utilizing *E. coli* as the host was employed as the protein to be secreted.

The pUB 110 was incised with the restriction enzyme Bam HI, treated with *E. coli* DNA polymerase I (Klenow fragment) in a conventional manner, incorporated with the Hind III linker and incised with the Hind III followed by 0.8% agarose gel electrophoresis to thereby extract DNA, which was used as the vector, in the same manner as mentioned above.

The pBR 322 was sufficiently incised with the restriction enzyme Eco RI and further incised with exonuclease Bal 31 (a product of BRL) for approximately 30 seconds.

The resultant was precipitated with ethanol to concentrate and purify the DNA and then sufficiently incised with a restriction enzyme Bst NI (a product of New England Bio Labs.) again. Then it was subjected to 1.2% agarose gel electrophoresis and DNA was cut out in the vicinity of 1.4 to 1.5 Kbp and extracted from the gel by the hydroxyapatite method. The extract was blunt-ended with the *E. coli* DNA polymerase I (a product of Takara Shuzo Co., Ltd.) and dNTP (a product of Yamasa Shoyu Co., Ltd.). The resultant was linked with the Hind III linker and incised with the Hind III. Said fragment was cut out by 1.2% agarose gel electrophoresis to give the DNA fragment coding for the ampicillin-decomposing enzyme to which the peptide derived from the Hind III linker was added at the N-terminal.

3. Secretion of ampicillin-decomposing enzyme

The three fragments, namely, the vector as obtained above, the DNA fragment coding for the ampicillin-decomposing enzyme and B-31 or B-41 were mixed in approximately equal amounts and the mixture was linked with T4 ligase and introduced into the *Bacillus subtilis* protoplast in a conventional manner. After regeneration, it was cultured in a medium containing 10 μg/ml of kanamycin to thereby obtain each transformed strain capable of growing in said medium.

Among these strains, those producing the ampicillin-decomposing enzyme were selected by taking advantage of the fact that they would make red halo by spraying a nitrocefin solution (Ohmura, K., et al., J. Biochem., 95, 87–93 (1984)). Each isolated strain derived from B-31 or B-41 was cultured in an L-broth containing 10 μg/ml of kanamycin. Consequently the ampicillin-decomposing enzyme was found in each medium. The activity of the enzyme was determined in a reaction system wherein nitrocephine was employed as the substrate (O'Callaghan, A. H., Morris, A., Kirby, S. M., and Shingler, A. H., Antimicrob. Agents Chemother., 1, 283–288 (1972)).

The enzyme secreted in the medium was precipitated and concentrated with a TCA solution in a conventional manner and the molecular weight thereof was determined with a 10% SDS polyacrylamide gel. As a result, a protein of with a molecular weight of approximately 27,200 and that of approximately 28,200 were detected from B-31 and B-41, respectively. The molecular weight (i.e. approximately 27,200) of the former protein roughly coincided with the total molecular weight of the ampicillin-decomposing enzyme itself and several amino acids coded by the Hind III linker. On the other hand, the molecular weight (i.e. approximately 28,200) of the latter protein was higher than that of the former by approximately 1,000, which suggested that the protein obtained from B-41 comprised other peptide as well as the ampicillin-decomposing enzyme and several amino acids coded by the Hind III linker. In addition, the system utilizing B-31 produced a larger amount of the ampicillin-decomposing enzyme than that utilizing B-41.

Consequently it has been found that production of proteins by the use of a signal peptide comprising the DNA coding for the signal peptide of the present invention to which further DNA was added would result in the secretion of the protein carrying unincised parts of the signal peptide at the upstream of the N-terminal as well as a lower productivity than that of the system utilizing the signal peptide of the present invention.

In the culture of *Bacillus subtilis* in the above Preparation and Experimental Examples, a modified L-broth containing 1 g/100 ml of Bacto tryotone (a product of Difco), 0.5 g/100 ml of Yeast Extract (a product of Difco), 1.0 g/100 ml of NaCl and 0.2 g/100 ml of glucose and adjusted to a pH value of 7.0 was used in the preparation of *p*11, while a similar modified L-broth containing 0.5 g/100 ml of NaCl was used in other cases. Each culture was carried out under shaking. The buffer solutions used in the enzyme reaction, electrophoresis and DNA extraction herein were all those having usual compositions found in relevant manuals, various literature or guide books.

The reactions with restriction enzymes and other enzymes as described in Preparation and Experiment Examples were carried out according to manufacturers' directions.

What is claimed is:

1. Essentially pure DNA consisting essentially of a sequence of DNA bases coding for the signal amino acid sequence:

| Met | Phe | Ala | Lys | Arg | Phe | Lys |
|-----|-----|-----|-----|-----|-----|-----|
| Thr | Ser | Leu | Leu | Pro | Leu | Phe |
| Ala | Gly | Phe | Leu | Leu | Leu | Phe |
| Tyr | Leu | Val | Leu | Ala | Gly | Pro |
| Ala | Ala | Ala. | | | | |

2. Essentially pure DNA as set forth in claim 1, wherein the sequence of DNA bases coding for the signal amino acid sequence is:

| ATG | TTT | GCA | AAA | CGA | TTC | AAA |
|-----|-----|-----|-----|-----|-----|-----|
| ACC | TCT | TTA | CTG | CCG | TTA | TTC |
| GCT | GGA | TTT | TTA | TTG | CTG | TTT |
| TAT | TTG | GTT | CTG | GCA | GGA | CCG |
| GCG | GCT | GCG. | | | | |

3. A vector containing DNA consisting essentially of the sequence of DNA bases as set forth in claim 1.

4. A vector containing DNA consisting essentially of the sequence of DNA bases as set forth in claim 2.

5. Essentially pure DNA as set forth in claim 1, consisting of said sequence of DNA bases.

6. Essentially pure DNA as set forth in claim 2, consisting of said sequence of DNA bases.

* * * * *